United States Patent
Shabani et al.

(10) Patent No.: US 6,995,834 B2
(45) Date of Patent: Feb. 7, 2006

(54) METHOD FOR ANALYZING IMPURITIES IN A SILICON SUBSTRATE AND APPARATUS FOR DECOMPOSING A SILICON SUBSTRATE THROUGH VAPOR-PHASE REACTION

(75) Inventors: Mohammad B. Shabani, Tokyo (JP); Shigeru Okuuchi, Tokyo (JP)

(73) Assignee: Mitsubishi Materials Silicon Corp., Tokyo (JP)

(*) Notice: Subject to any disclaimer, the term of this patent is extended or adjusted under 35 U.S.C. 154(b) by 985 days.

(21) Appl. No.: 09/775,209

(22) Filed: Feb. 1, 2001

(65) Prior Publication Data

US 2002/0101576 A1 Aug. 1, 2002

(51) Int. Cl.
*G01N 1/00* (2006.01)

(52) U.S. Cl. .......................................... 356/36
(58) Field of Classification Search ............... 356/36, 356/244; 364/497; 422/243, 255, 129, 158; 73/866; 436/175, 182, 72, 807; 423/324, 423/336, 348
See application file for complete search history.

(56) References Cited

U.S. PATENT DOCUMENTS 5,849,597 A * 12/1998 Tokuoka et al. ............. 436/175
6,204,188 B1 * 3/2001 Abe et al. .................... 438/706

* cited by examiner

*Primary Examiner*—Tu T. Nguyen
(74) *Attorney, Agent, or Firm*—Reed Smith LLP

(57) ABSTRACT

A method for analyzing impurities present in a silicon substrate. The method includes the steps of accommodating a silicon substrate resting on a support, and a solution for decomposing a silicon substrate which comprises a mixture of hydrofluoric acid, nitric acid and sulfuric acid, in an air-tight reaction vessel, in such a way as to keep the silicon substrate from directly contacting with the decomposing solution; allowing the decomposing solution to vaporize, thereby causing the substrate to decompose through vapor-phase reaction for sublimation, without heating or pressurizing the reaction vessel; and recovering the residue left by the decomposed substrate, to analyze the impurities contained in the substrate. This method makes it possible to determine the content of impurities that are present in a silicon substrate extremely precisely in a comparatively short time by decomposing the substrate through vapor-phase reaction without resorting to heating or pressurization.

18 Claims, 3 Drawing Sheets

METHOD FOR ANALYZING IMPURITIES IN A SILICON SUBSTRATE AND APPARATUS FOR DECOMPOSING A SILICON SUBSTRATE THROUGH VAPOR-PHASE REACTION

BACKGROUND OF THE INVENTION

1. Field of the Invention

The present invention relates to a method for analyzing impurities in a silicon substrate represented by a silicon wafer, and an apparatus for decomposing a silicon substrate through vapor-phase reaction. More specifically, the present invention relates to a method for analyzing impurities in a silicon substrate without resorting to heating or pressurizing, and an apparatus for decomposing a silicon substrate through vapor-phase reaction.

2. Description of the Related Art

Metallic impurities contained in a silicon wafer cause leak current of the device to increase and the oxide membrane to degrade. Therefore, as the semiconductor device is more densely integrated to perform a higher function, impurities thereof come to have a greater impact on the performance of the device. To meet this situation, demand becomes acute for a method by which it is possible to directly evaluate the purity of a silicon wafer by dissolving the wafer itself with an acid and then analyzing the residue, instead of resorting to indirect assessment based on the measurement of electric properties of the wafer.

The known method for dissolving a silicon wafer includes direct and indirect methods: the former method (for example, M. Shabani et al., Proceedings of the Autumnal Meeting of the Japanese Society for Analytical Chemistry, 2H 09, p405 (1995)) consists of admixing a silicon wafer with an acid mixture of hydrofluoric acid and nitric acid so as to dissolve the wafer, and the latter method of vaporizing an acid mixture of hydrofluoric acid and nitric acid and applying the resulting gas to a wafer for decomposition. The indirect method is further classified into a method of pressurized decomposition and a method of non-pressurized decomposition.

Because the method of non-pressurized decomposition requires, for decomposition, a period as long as about five to ten days, and has been regarded as impractical, interest has been directed towards the method of pressurized decomposition. As such the method of pressurized decomposition, for example, Japanese Patent Laid-Open No. Hei 7-333121 (333121/1995) discloses a treatment method for high precision analysis of the impurities in a siliceous sample. The method consists of separately storing an analysis sample container in which a siliceous analysis sample is mounted and a decomposing solution comprising an acid mixture of hydrofluoric acid and nitric acid in a sealed vessel in such a way as to prevent the analysis sample from directly contacting with the solution; heating the vessel to cause the analysis sample to decompose into a sublimate; and recovering the residue in the analysis sample container.

This treatment method not only reduces the time necessary for analysis, but allows only a gas vaporized from the decomposition solution to contact with the analysis sample, and to decompose the analysis sample into a sublimate, because with this method the analysis sample and the decomposition solution are placed separately from each other in the vessel to avoid direct contact.

The above method based on pressurized decomposition, however, poses a number of problems: for the siliceous analysis sample to be safely decomposed into a sublimate in an atmosphere pressurized and heated, the vessel must be highly tightly sealed, and thus have walls with a considerable thickness of about 10–20 mm, particularly when the vessel is made of polytetrafluoroethylene (PTFE or Teflon (TM)). Moreover, because a large number of dew drops develop on the ceiling surface of the vessel, the vessel must have a dome-shaped ceiling in order to prevent dew drops from falling upon the sample.

SUMMARY OF THE INVENTION

An object of this invention is to provide a method for highly precisely analyzing impurities present in a silicon substrate in a comparatively short time by decomposing the substrate through vapor-phase reaction without resorting to heating or pressurization.

Another object of this invention is to provide a simply structured apparatus for decomposing a silicon substrate through vapor-phase reaction for which it is possible to use a reaction vessel not requiring tight sealing, and having comparatively thin walls and no domed-ceiling.

A first view-point of this invention is directed to a method for analyzing impurities present in a silicon substrate which comprises the steps of accommodating a silicon substrate resting on a support and a solution for decomposing the silicon substrate comprising a mixture of hydrofluoric acid, nitric acid and sulfuric acid in a tightly sealed reaction vessel in such a way as to keep the substrate from directly contacting with the solution; allowing the decomposing solution to vaporize without resorting to heating and pressurizing the vessel, and the vapor to decompose the silicon substrate into a sublimate; and recovering the residue left after decomposition of the substrate for the analysis of impurities contained in that substrate.

The method according to the first view-point of this invention for analyzing impurities present in a silicon substrate includes the use of a decomposing solution which is obtained by adding sulfuric acid to an acid mixture of hydrofluoric acid and nitric acid, wherein sulfuric acid absorbs both moistures of hydrofluoric acid and nitric acid in the decomposing solution, and moisture in the closed space within the reaction vessel, thereby reducing the relative humidity of that closed space. This accelerates the vaporization of the decomposing solution and makes it possible to obviate the need for heating of the vessel or pressurization of the vessel's space. Then, highly concentrated HF—HNO$_3$ gas vaporized from the decomposing solution comes into contact with a silicon substrate mounted on a support, thereby decomposing the substrate into a sublimate in a comparatively short time.

A second view-point of this invention is directed to an apparatus for decomposing a silicon substrate through vapor-phase reaction which comprises a reaction vessel with a container to contain a solution for decomposing a silicon substrate and with a lid for tightly sealing the container, and a support consisting of a pillar resting on the bottom of the container and of a platform on the top of and integral with the pillar, the platform being kept above the surface of decomposition solution, and carrying a silicon substrate thereupon.

With the apparatus according to the second view-point of this invention for decomposing a silicon substrate through vapor-phase reaction, a silicon substrate is placed on the platform kept above the surface of decomposing solution, and thus the substrate, being kept from direct contact with the decomposition solution but exposed to a gas vaporized from the solution, is decomposed into a sublimate.

DETAILED DESCRIPTION OF EMBODIMENTS OF THE INVENTION

A first embodiment of this invention relates to a method for analyzing impurities present in a silicon substrate by decomposing the substrate through vapor-phase reaction, and to an apparatus for gaseous decomposition.

Figure 1:
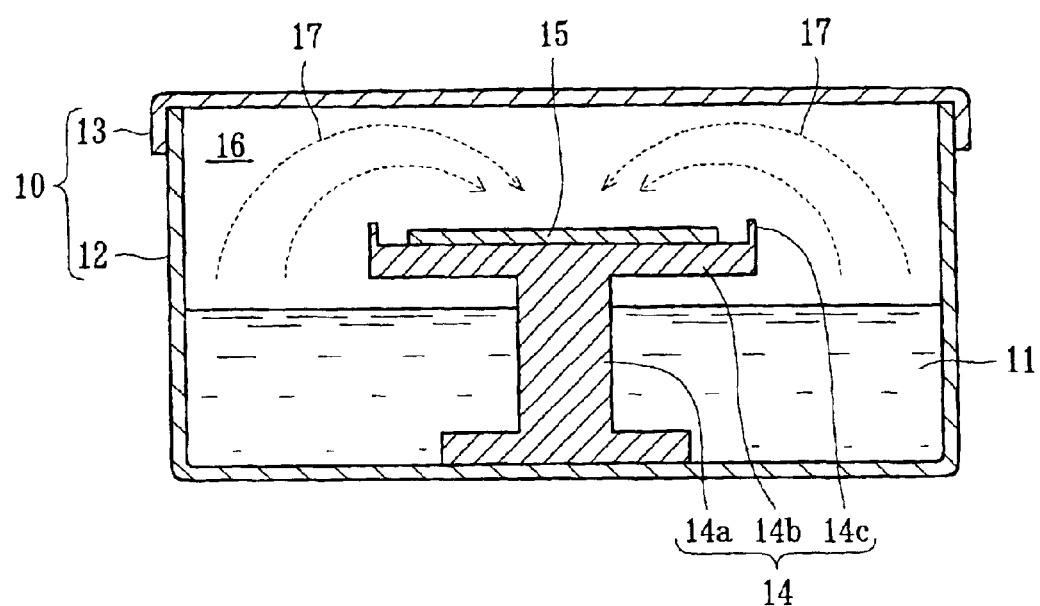
FIG. 1 is a sectional view of an apparatus representing a first embodiment of this invention to illustrate how a silicon substrate is decomposed through vapor-phase reaction.
Figure 2:
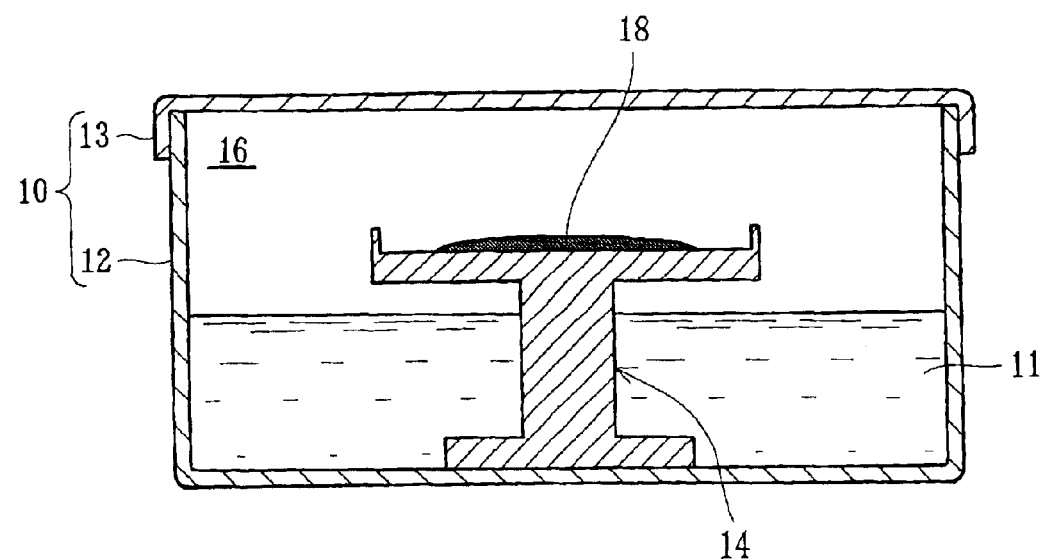
FIG. 2 is the same sectional view of the apparatus to illustrate the situation on completion of the decomposition.

A reaction vessel 10 comprises a container 12 to contain a solution 11 for decomposing a silicon substrate, and a lid 13 for tightly sealing the container 12 as shown in FIGS. 1 and 2. The container 12 and lid 13 are made of a plastic such as polypropylene (PP), or a fluorine-based resin like PTFE (Teflon), with a thickness of 1–3 mm, and together constitute a box. A support 14 is placed in the container 12. Because with this invention the reaction vessel 10 is not heated, the above-mentioned thickness of the container is sufficient not so as to deform the container even when the container contains the decomposing solution and the support. The support 14 is made of PTFE, and consists of a pillar 14a and a platform 14b. The pillar 14a rests on the bottom of container 12, protrudes above the surface of decomposing solution 11, and has a height about half that of the container 12. The platform 14b is on the top of and integral with the pillar 14a, and on the surface of the platform 14b is placed a silicon substrate 15. The platform 14b has a rim 14c on most part of its periphery. The container 12, lid 13 and support 14 must be thoroughly cleaned before they are used to decompose a silicon substrate. Because the decomposition of a silicon substrate according to this invention does not require heating, and takes place in a comparatively short time, dew drops which might develop on the inner surface of the lid 13 would be so small in volume that they would never fall on the substrate during its decomposition. Because of this, the inner surface of the lid does not need to be formed into a concave curvature.

A solution 11 for decomposing a silicon substrate is stored in the container 12 in such a way as to make its surface slightly lower than the platform 14b. Namely, if the volume of the reaction vessel 10 is taken to be 100%, the decomposing solution 11 is preferably stored in a volume ratio of 10–20% to the volume of the vessel 10. The decomposing solution 11 is prepared by adding sulfuric acid ($H_2SO_4$) to a mixture of hydrofluoric acid (HF) and nitric acid ($HNO_3$). To put it more specifically, the solution 11 is obtained by admixing an aqueous solution of 98 wt % or more $H_2SO_4$ with a mixture comprising aqueous solutions of 40–50 wt % HF and 50–70 wt % $HNO_3$ to give a weight ratio of $HF:HNO_3:H_2SO_4$=0.38–1.5:0.35 1.02:0.98–2.94. The ratio is preferably $HF:HNO_3:H_2SO_4$= 0.76–1.5:0.68–1.02:1.47–2.94.

The container 12 may contain one or two wide-mouthed containers (not illustrated here) for storing a decomposition solution instead of storing the solution on the bottom of container 12, and a support resting beside the containers. With this arrangement, it becomes possible to obviate the need for wiping off the decomposition solution from the support after the support has been removed from the vessel on completion of the decomposition of a silicon substrate.

The decomposition solution 11 is stored in the container 12, and a silicon substrate 15 is placed horizontally on the top surface of platform 14b as shown in FIG. 1. The lid 13 is placed over the container 12 to tightly seal the reaction vessel 10. Then, $H_2SO_4$ absorbs, in addition to moisture of HF and $HNO_3$ in the decomposing solution 11, moisture in the air within the closed space 16 of vessel 10, thereby reducing the relative humidity of that space. Reduced relative humidity accelerates the vaporization of the decomposing solution without deliberately heating the solution and pressurizing the sealed reaction vessel. Highly concentrated gas of HF—$HNO_3$ 17 vaporizing from the solution is brought into contact with the silicon substrate 15 placed on the top of platform 14b, and decomposes the substrate 15 into a sublimate in a comparatively short time as shown in FIG. 2.

Decomposition of a silicon substrate proceeds as follows.

Firstly, oxidation of Si by $HNO_3$ or $NO_2$ gas and release of $SiO_2$ into air by HF gas take place simultaneously as shown by formulae (1) and (2) below.

$$Si+4HNO_3 \rightarrow SiO_2+4NO+2H_2O \tag{1}$$

$$SiO_2+4HF \rightarrow SiF_4+2H_2O \tag{2}$$

There is no unstable gas in the reaction vessel, and NO gas in the reaction of formula (1) immediately reacts with oxygen gas in the reaction vessel as shown by formula (3) below.

$$2NO+O_2 \rightarrow 2NO_2 \tag{3}$$

Moisture produced as a result of the reaction of formulae (1) and (2) adheres to the inner surface of the reaction vessel to turn into minute dew drops there, and then $SiF_4$ gas reacts with water of dew drops as shown in formula (4) below to produce ortho-silicic acid ($H_4SiO_4$) or a gel-like substance

$$SiF_4+4H_2O \rightarrow H_4SiO_4+4HF \tag{4}$$

$NO_2$ gas and HF gas produced as a result of the reactions as shown by formulae (3) and (4) respectively, are used to repeat the reactions of formulae (1) and (2), and recycled use of $NO_2$ gas and HF gas leads to the reduced pressure in the reaction vessel. As shown by formulae (1) and (3), oxidation of Si by $HNO_3$ gas produces $NO_2$, but it also produces a minute volume of $NH_3$ gas.

Through gaseous and liquid decomposition worked by HF and $HNO_3$, 97% or more of Si decomposes to produce $SiF_4$ while 3% or less of Si produces di-ammonium-hexafluorosilicate (($NH_4)_2SiF_6$). This compound occurs as a white crystal. In the first embodiment, $(NH_4)_2SiF_6$ is left on the platform 14b as a residue 18 after a silicon substrate has been decomposed.

The support 14 is taken out from the reaction vessel 10, and a mixture of hydrochloric acid (HCl) and $HNO_3$ is applied dropwise to the residue 18 of substrate 15 on the platform 14b, to dissolve the residue. The resulting solution is collected-into a beaker (not illustrated) from a slit (not illustrated) of the rim 14c. The acid mixture above comprises, for example, aqueous solutions of 20 wt % HCl and 68 wt % $HNO_3$ at a ratio of 2:1. The acid mixture is dropwise applied at a rate of 0.5–1.0 ml for 1 g of the residue or test sample. The solution collected in a beaker is heated to 60–90° C., and then $(NH_4)_2SiF_6$ turns into hydrofluosilicic acid ($H_2SiF_6$) and silicon tetrafluoride ($SiF_4$) which sublimate in a comparatively short time to leave a residue consisting of impurities in the beaker. The decomposition residue 18 may be firstly collected in a beaker and then an acid mixture of HCl and $HNO_3$ may be added dropwise to the residue for dissolution. The impurities left on the beaker is submitted to atomic absorption spectrometry (AAS) or to inductively coupled plasma mass spectrometry (ICP-MS) for quantification.

Figure 3:
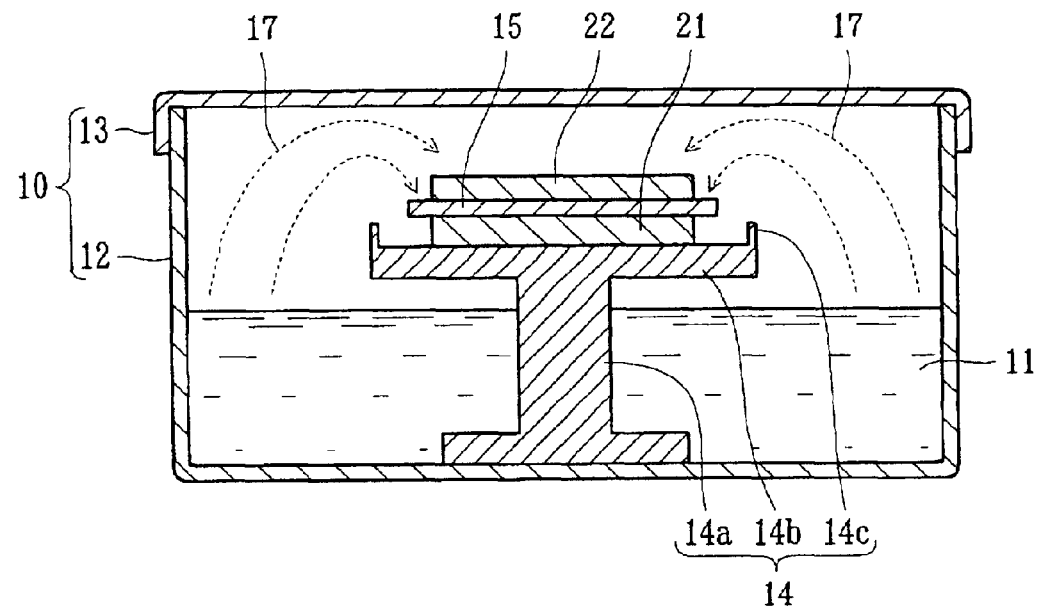
FIG. 3 is a sectional view of the apparatus of a second embodiment to illustrate how the periphery of a silicon substrate is decomposed through vapor-phase reaction.
Figure 4:
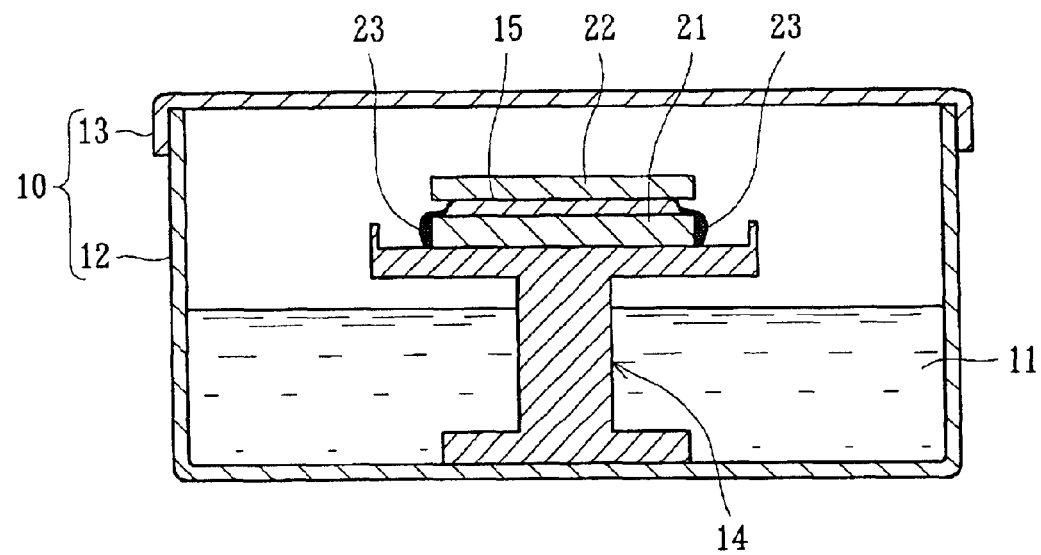
FIG. 4 is the same sectional view of the apparatus to illustrate the situation on completion of the decomposition.

Then, as a second embodiment another method for analyzing the impurities present on the periphery of a silicon wafer will be described with reference to FIGS. 3 and 4. In FIGS. 3 and 4, the same articles as those in FIGS. 1 and 2 are represented by the same symbols.

With this method, the silicon substrate 15 is represented by a silicon wafer; the wafer is inserted between two plates 21 and 22 made of a fluorine-based resin with the same size a little smaller than that of the wafer, in such a way as to allow its periphery to be exposed; and the whole assembly is placed on the platform 14b of support 14.

The periphery of wafer is exposed to highly concentrated HF—$HNO_3$ gas 17 in the reaction vessel 10 as shown in FIG. 3, so that only the exposed periphery is decomposed into a sublimate. The support 14 is taken out from the reaction vessel 10; the residue 23 as shown in FIG. 4 is collected into a beaker made of PTFE (not illustrated); and an acid mixture of HF and $HNO_3$ is added dropwise to the decomposition residue 23 in the beaker for dissolution. The acid mixture may be obtained by mixing aqueous solutions of 38 wt % HF and 68 wt % $HNO_3$ at a ratio of 2:1. The acid mixture may be added dropwise at a rate of 1.0 ml for 1 g of the residue or test sample. The solution collected in the beaker is heated to 150–220° C., and then the $(NH_4)_2SiF_6$ contained in the residue 23 turns into hydrofluosilicic acid ($H_2SiF_6$) and silicon tetrafluoride ($SiF_4$) which sublimate in a comparatively short time to leave a residue consisting of impurities in the beaker. The impurities left on the beaker is quantified by AAS or ICP-MS.

Figure 5:
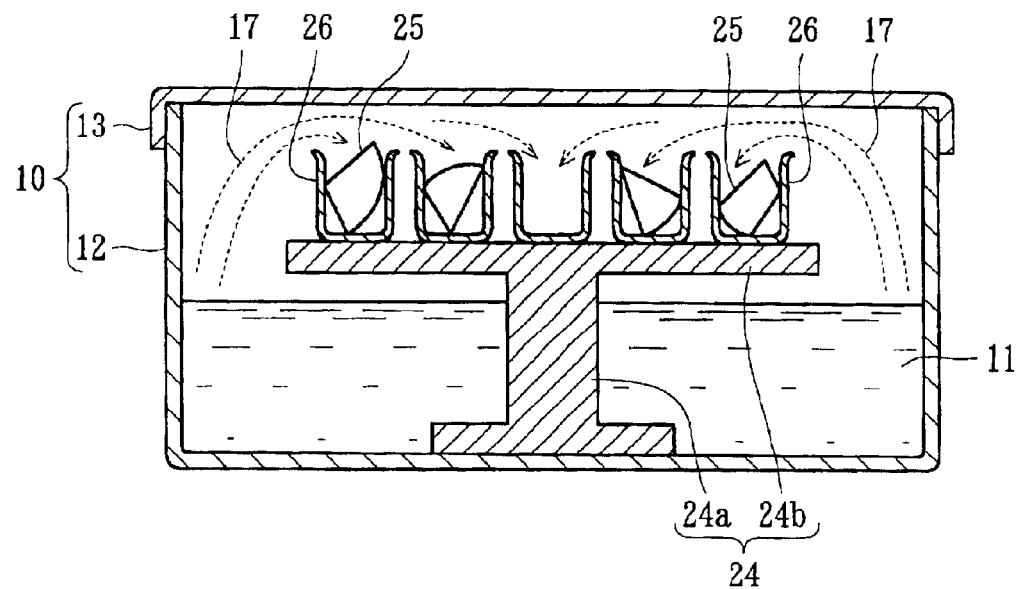
FIG. 5 is a sectional view of the apparatus of a third embodiment to illustrate how silicon substrates are decomposed through vapor-phase reaction in a manner different from above.
Figure 6:
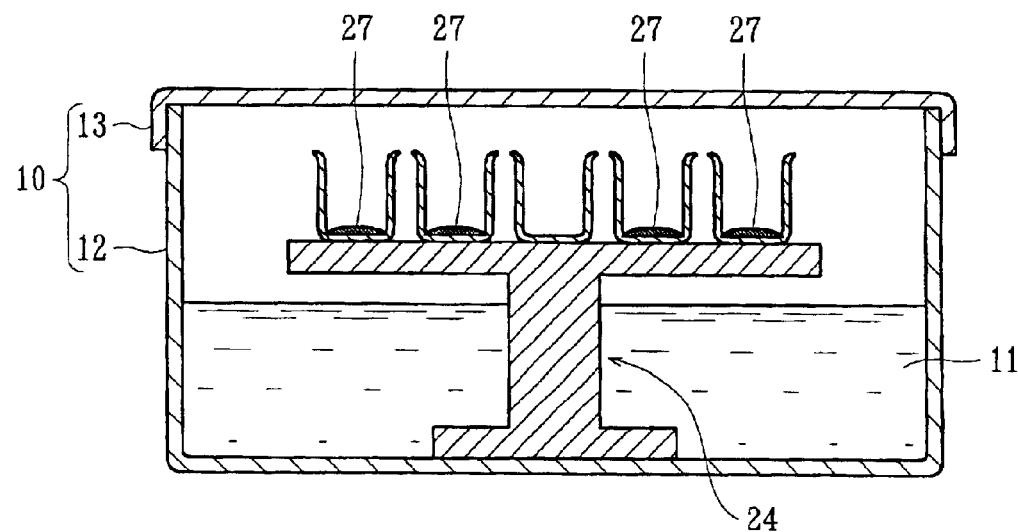
FIG. 6 is the same sectional view of the apparatus to illustrate the situation on completion of the decomposition.

Next, as a third embodiment a still other method for facilitating the recovery, dissolution and analysis of impurities will be described with reference to FIGS. 5 and 6. In FIGS. 5 and 6, the same articles as those in FIGS. 1 and 2 are represented by the same symbols.

With this method, the silicon substrate is represented by a silicon wafer; of five beakers made of PTFE, four beakers are allowed to contain fragments 25 of the wafer, and the remaining one beaker is left empty; and the beakers are placed on the platform 24b of support 24.

The wafer fragments 25 in the beakers 26 are exposed to highly concentrated HF—$HNO_3$ gas 17 in the reaction vessel 10 as shown in FIG. 5, to decompose into a sublimate. The support 24 is taken out from the reaction vessel 10; and an acid mixture obtained by mixing HCl and $HNO_3$ at the same ratio as described above is added dropwise to the residues 27 in the beakers as shown in FIG. 6 for dissolution. Hereupon, the acid mixture is also added to the beaker which carried no substrate fragment from the start. All five beakers are heated to 60–90° C.; in four out of the five beakers, $(NH_4)_2SiF_6$ contained in the residue 27 turns into hydrofluosilicic acid ($H_2SiF_6$) and silicon tetrafluoride ($SiF_4$) which sublimate in a comparatively short time to leave a residue consisting of impurities in the beaker. The residue left in the beaker which carried no substrate fragment from the start serves as a control. The test residues as well as the control residue are quantified by AAS or ICP-MS. Use of the control improves the accuracy of analysis.

The methods representing the embodiments of this invention for analyzing impurities present in a silicon substrate use a solution obtained by adding sulfuric acid to an acid mixture of hydrofluoric acid and nitric acid as a solution to decompose a silicon substrate into a sublimate. As a result, the methods enable high precision analysis of the impurities present in a silicon substrate comparatively rapidly by resorting to gaseous decomposition, thereby obviating the need for heating or pressurization.

Furthermore, the apparatus for decomposing a silicon substrate through vapor-phase reaction, because it is not exposed to heating or pressurization during the decomposition process, can have a simple structure: it needs not have thick walls nor highly tight seal, nor a concave-curved ceiling.

EMBODIMENT EXAMPLES

Next, embodiment examples of the present invention are explained together with comparative examples.

Embodiment Example 1

A 300 g of aqueous solution of 50 wt % HF and 200 g of aqueous solution of 68 wt % $HNO_3$ were placed in a PP container with a volume of 250 mm (length)×250 mm (width)×150 mm (height), and mixed there. To this acid mixture was gently added 300 g of aqueous solution of 98 wt % $H_2SO_4$ to prepare a decomposing solution. The weight ratio of the three components of the mixture was HF:$HNO_3$:$H_2SO_4$=0.77:0.7:1.52, and the mixture weighed 800 g. Then, a PTFE support was placed in the container. The platform of the support was at a level higher than the surface of decomposing solution. Five PTFE beakers were placed on the platform, and fragments of a silicon wafer each weighing about 1 g were put in four beakers, and the remaining one beaker was left empty. The fragments were prepared as follows: a silicon wafer was contaminated with Fe to give a concentration of $2\times10^{13}$ atoms/$cm^2$ on its surface, subjected to thermal treatment in a nitrogen atmosphere at 1000° C. for two hours, and cut into fragments. A PP lid of 2 mm thick was placed over the container to tightly seal the reaction vessel at room temperature. The presence of $H_2SO_4$ made it possible to decompose all the fragments in four beakers to sublimate in about 12 hours without having recourse to heating and pressurization.

An acid mixture obtained by mixing aqueous solutions of 20 wt % HCl and 68 wt % $HNO_3$ at a ratio of 2:1 was added dropwise to the residues of the decomposed fragments in the four beakers, at a rate of 1.0 ml for each 1 g of the residue for dissolution. The resulting solution was heated to 80° C. for 30 minutes, thereby allowing the residue to sublimate. To the empty beaker was also added dropwise the same amount of the acid mixture, and the solution was heated for vaporization. This served as the reference sample.

Comparative Example 1

A silicon wafer was dissolved by the direct dissolution method as proposed by M. Shabani et al., Proceedings of the Autumnal Meeting of the Japanese Society for Analytical Chemistry, 2H 09, p405 (1995). To put it more specifically, the same HF and $HNO_3$ solutions as used in Embodiment example 1 were mixed at a ratio of 0.76:0.70. A 20 g of the resulting acid mixture was placed in a PTFE beaker in which a 1 g fragment of a silicon wafer which had been deliberately contaminated with Fe in the same manner as in Embodiment example 1 was immersed. The beaker carrying the acid mixture immersing the 1 g wafer fragment was left for 30 minutes at room temperature, heated at 120° C. for one hour to allow the acid to vaporize, and heated again at 200° C. for one hour to allow the solid. residue to sublimate.

Comparative Evaluation

The residue of test beaker of Embodiment example 1 was quantitatively analyzed by ICP-Ms, considering the comparative sample. The residue of Comparative example 1 was similarly quantified by ICP-MS. The results from Embodiment example 1 and Comparative example 1 were the same: the Fe concentration was about $3.1 \times 10^{14}$ atoms/cm$^3$ for both. Through this finding it was demonstrated that the analytical method of Embodiment example 1 is sufficiently accurate to determine the impurities of a silicon substrate.

What is claimed is:

1. A method for analyzing impurities present in a silicon substrate comprising the steps of:
    accommodating a silicon substrate resting on a support, and a solution for decomposing a silicon substrate which comprises a mixture of hydrofluoric acid, nitric acid and sulfuric acid, in a tightly sealed reaction vessel, in such a way as to keep the silicon substrate from directly contacting with the decomposition solution;
    allowing the decomposing solution to vaporize, thereby causing the substrate to decompose through vapor-phase reaction for sublimation and leaving a residue of the decomposed substrate, without requiring the reaction vessel to be heated or pressurized; and
    recovering the residue left by the decomposing substrate, to analyze the impurities contained in the substrate.

2. A method according to claim 1 wherein the mixing ratio of hydrofluoric acid, nitric acid and sulfuric acid occurs at (0.38–1.5):(0.35–1.02):(0.98–2.94) by weight.

3. A method according to claim 2 further comprising the steps of:
    adding an acid mixture of hydrochloric acid and nitric acid to the recovered decomposition residue;
    heating the recovered decomposition residue with the acid mixture to 60–90° C., to allow the residue to sublimate; and
    quantitatively analyzing the remnants by atomic absorption spectroscopy or by inductively coupled plasma mass spectroscopy.

4. A method according to claim 2 further comprising the steps of:
    adding an acid mixture of hydrofluoric acid and nitric acid to the recovered decomposition residue;
    heating the recovered decomposition residue with the acid mixture to 150–220° C., to allow the residue to sublimate; and
    quantitatively analyzing the remnants by atomic absorption spectroscopy or by inductively coupled plasma mass spectroscopy.

5. A method according to claim 2 wherein the silicon substrate is a silicon wafer, the silicon wafer being inserted between two plates made of a fluorine resin having the same diameter which is a little smaller than that of the wafer, and the assembly being placed on the support.

6. A method according to claim 5 further comprising the steps of:
    adding an acid mixture of hydrochloric acid and nitric acid to the recovered decomposition residue;
    heating the recovered decomposition residue with the acid mixture to 60–90° C., to allow the residue to sublimate; and
    quantitatively analyzing the remnants by atomic absorption spectroscopy or by inductively coupled plasma mass spectroscopy.

7. A method according to claim 5 further comprising the steps of:
    adding an acid mixture of hydrofluoric acid and nitric acid to the recovered decomposition residue;
    heating the recovered decomposition residue with the acid mixture to 150–220° C., to allow the residue to sublimate; and
    quantitatively analyzing the remnants by atomic absorption spectroscopy or by inductively coupled plasma mass spectroscopy.

8. A method according to claim 2 wherein one or more fragments of a silicon substrate are put in one, or in two or more beakers made of a fluorine resin, and the beakers are placed on the support.

9. A method according to claim 8 further comprising the steps of:
    adding an acid mixture of hydrochloric acid and nitric acid to the recovered decomposition residue;
    heating the recovered decomposition residue with the acid mixture to 60–90° C., to allow the residue to sublimate; and
    quantitatively analyzing the remnants by atomic absorption spectroscopy or by inductively coupled plasma mass spectroscopy.

10. A method according to claim 8 further comprising the steps of:
    adding an acid mixture of hydrofluoric acid and nitric acid to the recovered decomposition residue;
    heating the recovered decomposition residue with the acid mixture to 150–220° C., to allow the residue to sublimate; and
    quantitatively analyzing the remnants by atomic absorption spectroscopy or by inductively coupled plasma mass spectroscopy.

11. A method according to claim 1 further comprising the steps of:
    adding an acid mixture of hydrochloric acid and nitric acid to the recovered decomposition residue;
    heating the recovered decomposition residue with the acid mixture to 60–90° C., to allow the residue to sublimate; and
    quantitatively analyzing the remnants by atomic absorption spectroscopy or by inductively coupled plasma mass spectroscopy.

12. A method according to claim 1 further comprising the steps of:
    adding an acid mixture of hydrofluoric acid and nitric acid to the recovered decomposition residue;
    heating the recovered decomposition residue with the acid mixture to 150–220° C., to allow the residue to sublimate; and
    quantitatively analyzing the remnants by atomic absorption spectroscopy or by inductively coupled plasma mass spectroscopy.

13. A method according to claim 1 where the silicon substrate is a silicon wafer, the silicon wafer being inserted between two plates made of a fluorine resin having the same diameter which is a little smaller than that of the wafer, and the assembly being placed on the support.

14. A method according to claim 13 further comprising the steps of:
adding an acid mixture of hydrochloric acid and nitric acid to the recovered decomposition residue;
heating the recovered decomposition residue with the acid mixture to 60–90° C., to allow the residue to sublimate; and
quantitatively analyzing the remnants by atomic absorption spectroscopy or by inductively coupled plasma mass spectroscopy.

15. A method according to claim 13 further comprising the steps of:
adding an acid mixture of hydrofluoric acid and nitric acid to the recovered decomposition residue;
heating the recovered decomposition residue with the acid mixture to 150–220° C., to allow the residue to sublimate; and
quantitatively analyzing the remnants by atomic absorption spectroscopy or by inductively coupled plasma mass spectroscopy.

16. A method according to claim 1 wherein one or more fragments of a silicon substrate are put into one, or in two or more beakers made of a fluorine resin, and the beakers are placed on the support.

17. A method according to claim 16 further comprising the steps of:
adding an acid mixture of hydrochloric acid and nitric acid to the recovered decomposition residue;
heating the recovered decomposition residue with the acid mixture to 60–90° C., to allow the residue to sublimate; and
quantitatively analyzing the remnants by atomic absorption spectroscopy or by inductively coupled plasma mass spectroscopy.

18. A method according to claim 16 further comprising the steps of:
adding an acid mixture of hydrofluoric acid and nitric acid to the recovered decomposition residue;
heating the recovered decomposition residue with the acid mixture to 150–220° C., to allow the residue to sublimate; and
quantitatively analyzing the remnants by atomic absorption spectroscopy or by inductively coupled plasma mass spectroscopy.

* * * * *